US009040664B2

(12) United States Patent
Hinds et al.

(10) Patent No.: US 9,040,664 B2
(45) Date of Patent: May 26, 2015

(54) MATERIALS AND METHODS FOR PREPARING PROTEIN-POLYMER CONJUGATES (75) Inventors: Kenneth Hinds, Erdenheim, PA (US); Danny Lewis, Hartselle, AL (US); Paul Schmidt, Niwot, CO (US); Kathleen M. Campbell, Longmont, CO (US)

(73) Assignee: AntriaBio, Inc., Louisville, CO (US)

(*) Notice: Subject to any disclaimer, the term of this patent is extended or adjusted under 35 U.S.C. 154(b) by 1806 days.

(21) Appl. No.: 10/553,570

(22) PCT Filed: Apr. 8, 2004

(86) PCT No.: PCT/US2004/010995
§ 371 (c)(1),
(2), (4) Date: Aug. 22, 2006

(87) PCT Pub. No.: WO2004/091494
PCT Pub. Date: Oct. 28, 2004

(65) Prior Publication Data
US 2007/0083006 A1    Apr. 12, 2007

Related U.S. Application Data (60) Provisional application No. 60/462,364, filed on Apr. 11, 2003.

(51) Int. Cl.
*A61K 38/00* (2006.01)
*C07K 14/62* (2006.01)
*A61K 47/48* (2006.01)
*A61K 9/50* (2006.01)
*A61K 38/28* (2006.01)

(52) U.S. Cl.
CPC ........... *C07K 14/62* (2013.01); *A61K 47/48215* (2013.01); *A61K 9/5031* (2013.01); *A61K 38/28* (2013.01)

(58) Field of Classification Search
None
See application file for complete search history.

(56) References Cited

U.S. PATENT DOCUMENTS

| 4,179,337 | A | 12/1979 | Davis et al. | |
| 5,102,872 | A | 4/1992 | Singh et al. | |
| 5,320,840 | A | 6/1994 | Camble et al. | |
| 5,446,090 | A | 8/1995 | Harris | |
| 5,672,662 | A | 9/1997 | Harris et al. | |
| 5,880,255 | A | 3/1999 | Delgado et al. | |
| 5,942,253 | A | 8/1999 | Gombotz et al. | |
| 5,985,265 | A | * | 11/1999 | Kinstler et al. | 424/85.4 |
| 6,323,311 | B1 | 11/2001 | Liu et al. | |
| 6,586,398 | B1 | * | 7/2003 | Kinstler et al. | 514/7.7 |
| 6,706,289 | B2 | * | 3/2004 | Lewis et al. | 424/501 |
| 2002/0155158 | A1 | 10/2002 | Lewis et al. | |

FOREIGN PATENT DOCUMENTS

| EP | 0027161 A1 | 4/1981 |
| EP | 1613272 | 12/2013 |
| WO | WO-98/46212 A1 | 10/1998 |
| WO | 02/36169 A2 | 5/2002 |
| WO | WO-02/41829 A2 | 5/2002 |

OTHER PUBLICATIONS

Hinds et al. (Advanced Drug Delivery Reviews, vol. 54, 2002, pp. 505-530).*
Hinds et al. (Bioconjug. Chem., Mar.-Apr. 2000, vol. 11, No. 2, pp. 195-201).*
Uchio et al (Advanced Drug Delivery Reviews, Elsevier BV, Amsterdam, NL, vol. 35, No. 2-3, Jan. 1, 1999, pp. 289-306).*
Uchio et al. (Advan. Drug Delivery, vol. 35, 1999, pp. 289-306).*
Hinds et al.(Advan. Drug Delivery, vol. 54, 202, pp. 505-530).*
Bentley, M. et al., "PEG Biphalin: A Potent Long-Acting Analgesic," *28th International Symposium on Controlled Release of Bioactive Materials*, pp. 1287-1288 (2001).
Diwan, M. et al., "Pegylation Enhances Protein Stability During Encapsulation in PLGA Microspheres," *Journal of Controlled Release*, 73:233-244 (2001).
Diwan, M. et al., "Stabilization of Recombinant Interferon-α by Pegylation for Encapsulation in PLGA Microspheres," *International Journal of Pharmaceutics*, 252:111-122 (2003).
Hinds, K.D. et al., "PEGylated Insulin in PLGA Microparticles. In vivo and in vitro Analysis," *Journal of Controlled Release*, 104:447-460 (2005).
Hora, M.S. et al, "Development of a Controlled Release Microsphere Formulation of Interleukin-2," *Proceedings of the 16th International Symposium on Controlled Release of Bioactive Materials*, 16:509-510 (1989).
Hora, M.S. et al., "Controlled Release of Interleukin-2 from Biodegradable Microspheres," *Bio/Technology*, 8:755-758 (1990).
Katre, N.V. et al., "Chemical Modification of Recombinant Interleukin 2 by Polyethylene Glycol Increases its Potency in the Murine Meth A Sarcoma Model," *Proc. Natl. Acad. Sci. USA*, 84:1487-1491 (1987).
Katre, N.V., "Immunogenicity of Recombinant IL-2 Modified by Covalent Attachment of Polyethylene Glycol," *The Journal of Immunology*, 144(1):209-213 (1990).
Kim, B.M. et aL, "Controlled Release of Pegylated Peptides from Poly(Lactic-Co-Glycolic Acid) Microspheres," *Proceed. Int'l. Symp. Control. Rel. Bioact. Mater.*, No. 6175:960-961 (2001).

(Continued)

*Primary Examiner* — Hope Robinson
(74) *Attorney, Agent, or Firm* — Kilpatrick Townsend & Stockton LLP (57) ABSTRACT

The invention is directed to a single-step method for rapidly and efficiently preparing protein-polymer conjugates, including an insulin-polymer conjugate. According to the method of the present invention, a protein and hydrophilic polymer are contacted in the presence of at least one organic solvent and at least one metal chelator, under conditions that promote the formation of a conjugate of the protein and polymer. Thus, the invention is directed to the site-specific modification of selected proteins, such as insulin, with poly(ethylene glycol) at residue PheB1. The invention also provides a pharmaceutical formulation for encapsulating the conjugate in a biodegradable polymer.

10 Claims, 6 Drawing Sheets

(56) References Cited

OTHER PUBLICATIONS

Kim, T.H. et al, "Pegylated Recombinant Human Epidermal Growth Factor (rhEGF) for Sustained Release from Biodegradable PLGA Microspheres," *Biomaterials*, 23:2311-2317 (2002).

Lam, X.M. et al., "Sustained Release of Pegylated Monoclonal Antibody Fragments from Drug Delivery Systems," *Controlled Release Society 29th Annual Meeting Proceedings*, No. 037 (2002).

Lam, X.M. et al., "Integrity of PEGylated Monoclonal Antibody Fragment in Polymeric Matrices," *Controlled Release Society 30th Annual Meeting Proceedings*, No. 449 (2003).

Misicka, A. et al., "Structure-Activity Relationship of Biphalen. The Synthesis and Biological Activities of New Analogues with Modifications in Positions 3 and 4," *Life Sciences*, 60(15):1263-1269 (1997).

Yip, C.M. et al., "Direct Force Measurements of Insulin Monomer-Monomer Interactions," *Biochemistry*, 37:5439-5449 (1998).

International Search Report Application No. PCT/US04/10995, dated Dec. 1, 2005.

De Rosa, G. et al, "Influence of the co-encapsulation of different non-ionic surfactants on the properties of PLGA insulin-loaded microspheres," Journal of Controlled Release, 2000, vol. 69, p. 283-295.

Canadian Intellectual Property Office, Official Action for Application No. 2,521,381 mailed on Mar. 20, 2013, 3 pages.

Chinese Patent Office, Official Action for Application No. 200810131122.9 mailed on Apr. 11, 2013, 30 pages.

Liu, F. et al., "Glucose-induced release of glycosylpoly (ethylene glycol) insulin bound to a soluble conjugate of concanavalin A", Bioconjug. Chem., 8, Pates 664-672, 1997.

Yeh, M. K., "The stability of insulin in biodegradable microparticles based on blends of lactide polymers and polyethylene glycol", J. Microencapsul., 17, pp. 743, 756, 2000.

Office Action in related Canadian application No. 2521381 issued on Apr. 1, 2014, 3 pages.

Hinds, K. D. et al., "Effects of PEG conjugation of insulin properties", Advanced Drug Delivery Reviews, Elsevier BV, Amsterdam, NL, vol. 54, Jan. 1, 2002, pp. 505-530.

Hinds, K. D. et al., "Synthesis and characterization of poly(ethylene glocol)—insulin conjugates", Bioconjugate Chemistry, ACS, Washington, DC, Col. 11, Feb. 15, 2000, pp. 195-201.

Uchio, T. et al., "Site-specific insulin conjugates with enhanced stability and extended action profile", Advanced Drug Delivery Reviews, Elsevier, Amsterdam, vol. 35, No. 2-3, Jan. 1, 1999, pp. 289-306.

Extended Search Report of European Application No. 12190040 issued on Jun. 26, 2014, 10 pages.

* cited by examiner

SEQUENCE LISTING

<160> NUMBER OF SEQ ID NOS: 1

<210> SEQ ID NO 1
<211> LENGTH: 51
<212> TYPE: PRT
<213> ORGANISM: Homo sapiens

```
<400> SEQUENCE: 1

Gly Ile Val Glu Gln Cys Cys Thr Ser Ile Cys Ser Leu Tyr Gln Leu
 1               5                  10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50
```

MATERIALS AND METHODS FOR PREPARING PROTEIN-POLYMER CONJUGATES

RELATED APPLICATIONS

This application is a 371 of PCT/US04/10995 filed Apr. 8, 2004 and claims priority to U.S. Provisional Patent Application No. 60/462,364, entitled "Methods for Preparation of Site-Specific Protein Conjugates" filed on Apr. 11, 2003, the entire contents of which are incorporated herein by reference.

FIELD OF THE INVENTION

The invention relates to chemically modified protein conjugates that possess superior properties to those of the unconjugated protein. Specifically, the invention relates to a greatly simplified, cost effective and process scalable method for the modification of proteins with hydrophilic polymers. More specifically, the invention relates to the site-specific modification of selected proteins, such as insulin, with poly(ethylene glycol). The invention also relates to biodegradable polymer-based drug delivery formulations comprising proteins having site-specific modifications with hydrophilic proteins.

DESCRIPTION OF THE RELATED ART

A variety of methods for producing PEGylated insulin derivatives are known. Davis et al. (U.S. Pat. No. 4,179,337) described the synthesis of a PEG-insulin construct using trichloro-s-triazine (cyanuric chloride) as the linker between PEG and protein. They followed a synthetic scheme in which a large excess (50×) of cyanuric chloride activated PEG (2000 Da) was reacted with insulin in borate buffer (pH 9.2) for 2 hours. The inventors were able to produce partially active (~50%) PEG-insulin conjugates, which were non-immunogenic and non-antigenic. Obermeier et al. (Canadian Patent No. 1,156,217), found that preparation of PEG-insulin conjugates according to Example X of the Davis patent referenced above produced a non-uniform mixture of conjugates containing approximately 50% tri-PEG-insulin, and the other possible PEG-insulin derivative combinations (mono- and di-PEG-insulins) were not substituted at residue PheB1.

Obermeier et al. (Canadian Patent No. 1,156,217) describe a synthesis of PEG-insulin conjugates specifically modified at residue PheB1. The basis of their invention involves protecting the reactive amines at residues GlyA1 and LysB29 with tert-butyloxycarbonyl (t-boc) or methylsulfonylethyloxycarbonyl (Msc) groups in organic solvents (e.g., DMF, DMSO, pyridine, etc.) under alkaline conditions. From the complex mixture of (mono-, di-, and tri-) protected insulins the $N^{\alpha A1}$, $N^{\epsilon B29}$-bis-protected-insulin species was isolated by conventional chromatographic techniques. Following isolation, the pure $N^{\alpha A1}$, $N^{\epsilon B29}$-bis-protected-insulin was reacted with an activated (e.g., acid chloride or isocyanate) PEG derivative with subsequent removal of the protecting groups using techniques common to peptide chemistry. The inventors observed that the amino groups of GlyA1 and LysB29 were more reactive than PheB1's amino group under alkaline reaction conditions. They determined their site-specific mPEG(1500)-B1-insulin conjugates had a 100% insulin effect (calculated on a molar basis) on reduction of blood sugar levels in rabbits.

Geiger et al. (in D. Branderburg, and A. Wollmer (eds.), Insulin: Chemistry, Structure, and Function of Insulin and Related Hormones, Walter de Gruyter & Co., New York, pp. 409-415, 1980) and Ehrat et al. (Biopolymers, 22, 569-573, 1983) describe PEG-insulin adducts specifically modified at residue PheB1 prepared utilizing a protection/conjugation/deprotection scheme similar to the multi-step method described by Obermeier et al. Geiger et al. and Ehrat et al. observed that the PEG(1500)-B1-insulin conjugate was far less antigenic and far more stable (to liver enzymes) than native insulin. Other PEG-insulin preparations (Caliceti et al., STP Pharma Sci, 9, 107-113 1999; Uchio et al., Advanced Drug Delivery Reviews, 35, 289-306, 1999; Hinds et al., Bioconj. Chem. 11, 195-201, 2000; Hinds et al., Advanced Drug Delivery Reviews, 54: 505-530, 2002) are either: 1) centered on the basic three-step protection/conjugation/deprotection schemes outlined above, 2) result in non-specific modification of the insulin molecule, or 3) do not produce the most effective conjugates, namely, PEG-B1-insulins.

Liu et al. (U.S. Pat. No. 6,323,311 B1) describe a useful method for the synthesis of PEG-B1-insulin conjugates. This method is an extension of the Obermeier three-step protection/conjugation/deprotection scheme, but does not require the isolation of reaction intermediates between steps (i.e., one-pot synthesis). Thus, the insulin is protected at residues GlyA1 and LysB29, immediately reacted with PEG, and subsequently deprotected before any isolation of species. The inventors claim that their one-pot reaction may yield up to 50% of the correct positional isomer (i.e. PEG-B1-insulin) and 30% unreacted insulin that can be recycled for subsequent derivatization. Assuming the preparation of these constructs is carried out expeditiously, it would take at least five days to completion. In addition, the invention requires large excesses of the PEG reagent to achieve acceptable results. While the products of this invention may be effective, their preparation still requires the protein to undergo three reaction steps in protein-adverse environments (high and low pH) for extended periods of time.

The present invention addresses the shortcomings of prior art methods for PEGylating insulins by providing a method for the simple preparation of highly pure insulin derivatives specifically PEGylated at the N-terminus of insulin's B-chain (PheB1) in a single-step. In contrast to prior experience (e.g., Caliceti et al., 1999, supra) indicating that PEGylation at PheB1 is the least probable reaction product, the present method employs specific conditions of pH control, use of a metal ion chelator and addition of organic solvent to enhance the relative reactivity of the PheB1 amino terminus to where it becomes the predominant site of PEGylation. Considering the numerous beneficial properties imparted on insulin (e.g., decreased immunogenicity/antigenicity; increased proteolytic, chemical and physical stability; increased circulation half-life; increased aqueous/organic solubility; full biological activity) via site-specific PEGylation at residue PheB1, a simple, cost-effective, and easily scalable process for achieving this result would be a significant advancement in the art.

SUMMARY OF THE INVENTION

The present invention is based on the discovery of a single-step method for preparing protein-polymer conjugates. The invention also relates to biodegradable polymer-based drug delivery formulations comprising proteins having site-specific modifications with hydrophilic proteins. In a particular embodiment, the present invention provides a single-step method for synthesis of PEGylated insulin derivatives wherein the site of substitution is predominantly residue PheB1 (N-terminus of the B-chain). It is well known in the art that such derivatives are physically and enzymatically more stable than native insulin. In addition, the derivatives are more soluble in aqueous/organic systems than insulin. Moreover, these derivatives have been shown to be less immunogenic and to have prolonged circulation half-lives.

A significant advantage of the present invention is that the reaction takes place in near-neutral conditions where unwanted side-reactions (e.g., deamidation, transamidation, oxidation, etc.) are negligible. Another advantage is the use of relatively low amounts of polymer (e.g., PEG reagent), thus reducing costs. The resulting protein-polymer conjugate (e.g., PEGylated insulin) may be used by itself, for example, in human therapy, or it may be encapsulated in a sustained release delivery vehicle, such as that disclosed in U.S. Patent Application 2002/0155158.

Accordingly, in one embodiment, the present invention provides a method for preparing a protein-polymer conjugate by contacting an insulin protein with a hydrophilic polymer in the presence of at least one organic solvent and at least one metal chelator, under conditions whereby a conjugate of the protein and polymer is formed. The conjugate can then be isolated using a variety of standard techniques, such as column chromatography.

In a particular embodiment of the invention, the hydrophilic polymer is selected from the group consisting of polyethylene glycol, polyethylene glycol/polypropylene glycol copolymers, polyoxyethylated glycerol, and linear, branched and amino-reactive derivatives thereof. Suitable amino-reactive derivatives include, for example, aldehydes, N-hydroxy succinimide esters of PEG-carboxylic acids, PNP-carbonates, and benzotrizole terminated hydrophilic polymer derivatives. Typically, the hydrophilic polymer and insulin protein are present at a molar ratio of about 10:1-1:1.

Suitable organic solvents for use in the invention include a wide variety of known solvents including, but not limited to, water-miscible organic solvents, such as ethanol, methanol, DMSO, dioxane, DMF and NMP. Typically, the organic solvent is present at a concentration of about 0.1 to 10%.

Suitable metal chelators for use in the invention also include a wide variety of known compounds including, but not limited to, polyvalent (e.g., divalent) metal ion chelators, such as EDTA, deferoxamine (DEF), diethylenetriamine pentaacetic acid (DTPA), and bis(aminoethyl)glycolether N,N, N',N'-tetraacetic acid (EGTA). Generally, the chelator is present at a concentration from about 0.1-10 mM.

In a particular embodiment of the invention, the insulin protein and hydrophilic polymer (e.g., PEG) are contacted (i.e., reacted or conjugated) in an aqueous solution at a protein concentration of about 0.1-5% by weight. In another embodiment of the invention, the insulin protein and hydrophilic polymer are contacted in an aqueous solution at a pH of about 5.0-7.5, preferably about 7.0. This results in a yield of up to 50% of the correct positional isomer of insulin-polymer conjugate. In another particular embodiment, the hydrophilic polymer and insulin protein are contacted at a temperature of about 4° C. to 50° C., preferably about 15° C. to 25° C.

Once formed, the protein-polymer conjugate is then separated from unwanted side reaction products and unreacted insulin protein. This can be achieved using a variety of known techniques, such as chromatography. In a particular embodiment, ion exchange chromatography is employed.

In yet another embodiment, the method of the present invention further comprises the step of quenching the reaction (i.e., conjugation) of insulin protein and hydrophilic polymer, prior to isolating the conjugation product. In a particular embodiment, this is achieved by reducing the pH of the reaction to about 1-4.

Particular protein-polymer conjugates produced by the methods of the present invention include, for example, insulin-polymer conjugates, preferably, insulin-PEG conjugates (PEGylated insulin). This can include any insulin or insulin-related protein, such as human insulin having the sequence shown in SEQ ID NO:1 and related family members. In a particular embodiment, the insulin is specifically reacted (PEGylated) at residue PheB1, without significant reaction at residues GlyA1 or LysB29. The resulting PEGylated insulin can be administered therapeutically in any suitable formulation as is well known in the art. In a particular embodiment, the conjugate is administered in a sustained release formulation by, for example, encapsulating the conjugate in a biodegradable polymer prior to administration.

Other embodiments of the present invention will be apparent from the following Detailed Description and Examples.

DETAILED DESCRIPTION

The present invention is directed to a single-step method for rapidly and efficiently preparing protein-polymer conjugates. The method includes reacting a protein and a hydrophilic polymer in the presence of at least one organic solvent and at least one metal chelator, under near-neutral conditions. Particular protein-polymer conjugates of the invention include insulin, PEGylated at the PheB1 amino terminus using minimum PEG reagent and mild conditions. Whereas prior work has shown that PheB1 is normally the least reactive amino group of insulin towards sterically "bulky" macromolecular reagents (see, e.g., Caliceti et al., 1999, supra), surprisingly, the methods of the present invention produce conditions in which PheB1 is the most reactive group available for modification with hydrophilic polymers. This allows for a simple, one-step reaction in which insulin PEGylated at PheB1 is the highest yield product, and can be separated from the other conjugates and unreacted insulin. The latter may be recycled for further conjugation if desired. The PEGylated PheB1 insulin conjugate retains full activity as measured by blood glucose control and the protein native structure is preserved.

Hydrophilic Polymers

The term "hydrophilic polymer" refers to any water-soluble linear, branched, forked, branched-forked, dendrimeric, multi-armed, or star-shaped polymer including, but not limited to, polyethylene glycol and polyethylene glycol/ polypropylene glycol copolymers, polyoxyethylated glycerol, and similar polymers. Preferably, the molecular weight of the polymer ranges from about 500 daltons to about 50,000 daltons. Hydrophilic polymers for use in the invention typically have at least one reactive group incorporated for attachment to the bioactive molecule of interest through amino, carboxyl, sulfhydryl, phosphate or hydroxyl functions. Hydrophilic polymers used in the present invention, such as polyethylene glycol, can be prepared according to standard protocols with one end capped as with a methoxy group and the other end activated for facile conjugation to active groups on bioactive molecules. For example, U.S. Pat. No. 6,113,906 describes the use of succinimidyl succinate or succinimidyl carbonate reactive groups on a "U-shaped" (i.e., branched) form of polyethylene glycol for reaction with the amino groups of proteins. U.S. Pat. No. 5,650,234 describes the use of N-hydroxybenzotriazole carbonate, 2-hydroxypyrimidine carbonate, and N-hydroxy-2-pyrrolidinone carbonate derivatives of polyethylene glycol for reaction with the amino groups of proteins to form a stable urethane bond. U.S. Pat. No. 5,672,662 describes the use of succinimidyl esters of propionic and butanoic acid substituted polyethylene glycols for reaction with the amino groups of proteins to form a stable amide bond. U.S. Pat. No. 5,446,090 describes the use of vinyl-sulfone derivatives of polyethylene glycol to form stable thioether bonds with the sulfhydryl groups of proteins. U.S. Pat. No. 5,880,255 describes the use of tresyl (2,2,2,-trifluoroethane-sulphonyl) derivatives of polyethylene glycol for reaction with the amino groups of proteins to form a simple, stable secondary amine linkage. U.S. Pat. No. 5,252,714 describes the use of propionaldehyde derivatives of polyethylene glycol for reaction with the amino groups of proteins resulting in a stable secondary amine bond. The bonds resulting from the attachment of such hydrophilic polymers to bioactive molecules can be intentionally designed to be stable or unstable (i.e., reversible). In addition, hydrophilic polymers used in the present invention can be prepared according to standard protocols with two similar (e.g., homobifunctional) or dissimilar (e.g., heterobifunctional) functional groups available to facilitate conjugation to active groups on bioactive molecules. For example, WO 126692A1 describes the use of heterobifunctional polyethylene glycol derivatives for protein modification. The entire contents of these patents are incorporated by reference herein.

In one embodiment, the hydrophilic polymer is poly (ethylene glycol) (PEG). PEG refers to a linear or branched neutral polyether with the chemical formula HO—$(CH_2CH_2O)_n$—H. PEG is highly soluble in water and many organic solvents (e.g., methylene chloride, ethanol, toluene, acetone, and chloroform), and is readily available in various sizes (molecular weights) and functionalized architectures (e.g., amino-, carboxyl-, and sulfhydryl-terminated). PEG has been found to be nontoxic and is approved by the FDA for use in drugs (parenterals, topicals, suppositories, nasal sprays), foods, and cosmetics. In solution PEG is a highly hydrated polymer, where each monomer (ethylene oxide unit) can bind up to three molecules of water. In addition, it is thought that PEG has the ability to influence the structure of several molecular layers of more loosely associated hydrating water molecules. Molecular simulations of the behavior of single surface-bound chains in water show the polymer exhibits a large degree of segmental flexibility. Thus, the polymer is assumed to occupy a large hydrodynamic volume in aqueous environments. These findings serve to explain why PEG is remarkably effective in excluding other polymers (natural and synthetic) from its presence. The exclusion of other polymers is the primary driving force behind PEG's ability to reject proteins, form two-phase systems with other synthetic polymers, and makes this polymer both nonimmunogenic and nonantigenic. When PEG is covalently attached to a protein, it typically transfers many of the polymer's favorable characteristics to the resultant conjugate. Because of the many beneficial properties mentioned above, PEG is well suited for protein modification.

As used herein, the term "PEG" includes any PEG polymer, including amino-reactive derivatives of PEG ("PEG reagents"). A variety of PEG reagents for protein conjugation are known. A typical PEG reagent is a linear PEG polymer with one end terminated in an ether linkage (e.g., O-methyl) and the other end functionalized with a reactive group. Other PEG reagents are branched or dendrimeric, again with a combination of non-reactive termini and reactive functional groups for linking to proteins. Alternatively, homo- or heterobifunctional PEG reagents with a combination of similar or dissimilar reactive functional groups may be used for linking to proteins. Examples of PEG reagents include, but are not limited to, an aldehyde, a N-hydroxy succinimidyl carbonate, a N-hydroxy succinimidyl propionate, a p-nitrophenyl-carbonate, or a benzotriazole-carbonate terminated species or other amino-reactive activated species of PEG.

The PEG polymer may have a molecular weight in the range of, for example, 500 to 50,000 Da. The reactive functional groups may be separated from the PEG chain by linker groups. Optionally, the polymers have degradable internal bonds between the PEG and linkers. Accordingly, in one embodiment of the invention, reactive groups on the PEG polymer may be electrophilically activated for reaction with protein nucleophiles. Examples of electrophilic groups are n-hydroxy succinimidyl carbonate, tresyl and aldehyde functionalities. PEG reagents with these functionalities will react to form covalent linkages to amino groups of proteins. A preferred PEG reagent for PEG conjugation to protein amino groups is the MPEG succinimidyl active ester of a propionic acid linker mPEG-SPA. Another preferred PEG reagent is monomethoxy PEG-aldehyde (mPEG-Ald).

Insulin-Polymer Conjugates

Parenteral administration of insulin formulations remains the primary therapy utilized for the treatment of insulin-dependent diabetes mellitus (IDDM) since insulin's discovery over 75 years ago. Many of the factors that make the current therapies inadequate are inherent shortcomings intrinsic to the insulin molecule. Specifically, insulin faces many problems typical to protein pharmaceuticals, including poor physical and chemical stability, susceptibility to proteolysis, immunogenicity and antigenicity, and a relatively short plasma half-life.

Protein PEGylation has been used to improve the therapeutic efficacy of recombinant human proteins. Most parenterally administered proteins are rapidly cleared from the body by the reticuloendothelial system (RES), kidney, spleen, and liver. Moreover, clearance depends on molecular size, charge, and the presence of specific cellular receptors for the proteins of interest. The attachment of PEG to a protein affects its molecular size, charge, and receptor-binding capabilities, which can serve to decrease the conjugate's overall rate of clearance.

In addition, the metabolism of proteins by enzymes leads to the rapid loss of biological activity of therapeutic proteins. By sterically shielding the protein domains susceptible to proteolytic attack, PEG decreases the protein degradation that renders it biologically inactive.

Moreover, even recombinant human proteins elicit immune responses after repeated use. By sterically masking the therapeutic protein's immunogenic/antigenic determinants, PEG-attachment commonly results in conjugates that are nonimmunogenic and nonantigenic. Accordingly, overall, the result of changes in the parental protein's characteristics by PEGylation increases the plasma half-life and resistance to proteolytic degradation and decreases immunogenicity and antigenicity of the resultant PEG-protein construct.

Insulin Protein

The term "insulin protein," as used herein, refers to any naturally occurring or recombinant insulin protein or related protein capable of being conjugated at, for example, residue PheB1. Accordingly, insulin proteins for use in the invention include, for example, insulin analogs, homologs and derivatives. Insulin from any suitable species can be used, such as human, pig, cow, dog, rat, mouse, sheep, or monkey. In a preferred embodiment, the insulin is human insulin.

Human insulin is a well-known protein, which is readily available commercially from a number of sources including, but not limited to, Sigma Chemical Company and Novo Nordisk. Naturally occurring human insulin is a protein having a molecular weight of approximately 5,500 daltons and includes approximately 51 amino acids. Depending on the manufacturer, the insulin may have slightly different activity based upon weight, however, the activity of insulin defined in units is the standard. Insulin having various degrees of biological activity is commercially available. For instance, it is possible to purchase low-, intermediate-, and rapid-acting forms of insulin. Non-insulin hypoglycemic agents that have similar activities to insulin or which increase insulin receptors include, but are not limited to, sulfonyl ureas (e.g., glibenclamide, gliclazide, glipizide, glyburide, chlorpropamide, tolbutamide, tolazamide, acetohexamide, and glimopride); thiazolidine diones (e.g., troglitazone and ploglitazone); alpha-glucosidase inhibitors (e.g., acarbose and miglitol); and third generation insulin-releasing agents (e.g., KAD 1220, etoxomir, and repaglinide).

The insulin molecule consists of two polypeptide chains, the A-chain and the B-chain. The amino acid sequence for human insulin is provided herein as SEQ ID NO:1. The A-chain is composed of 21 amino acids (denoted A1-A21), and the longer B-chain is comprised of 30 amino acids (B1-B30). These two chains are held together by two inter-chain disulfide bonds between residues A7 and B7, as well as, between A20 and B19, whereas another intra-chain disulfide bond connects residues A6 and A11. There are also numerous noncovalent interactions between the amino acid residues of the two chains that help to stabilize insulin into its three-dimensional structure.

There are three reactive amino groups available for modification (e.g., by PEG) namely, those located at the A- and B-chain N-termini (A1 and B1, respectively) and a lysine located adjacent to the B-chain C-terminus (B29).

Insulin proteins also include related proteins, such as the insulin-like growth factors (I and II), and proteins from the growth hormone/prolactin family.

Conjugation of Insulin Protein to Hydrophilic Polymer

In accordance with the present invention, the insulin protein and hydrophilic polymer are contacted (i.e., reacted or conjugated) in the presence of at least one organic solvent and at least one metal chelator, under conditions that promote the formation of a conjugate of the protein and polymer. In a particular embodiment, the insulin protein is PEGylated at the PheB1 amino terminus using minimum PEG reagent and mild conditions. The amino group of PheB1 is normally the least reactive of the 3 available amino functions on insulin (Caliceti et al., 1999, supra). In the present invention, conditions have been found that render the PheB1 amino group the most reactive to PEG reagents. These reaction conditions thus produce single PEGylation at the PheB1 as the predominant reaction product.

In a particular embodiment of the present invention, the insulin protein and hydrophilic polymer are contacted in an aqueous solution at a protein concentration of about 0.1 to 5% (w/w), preferably from 0.5-1.5%, adjusted to a pH in the range 5.0 to 7.5, preferably pH 6.5 to 7.2. The pH can be controlled by inclusion of buffer salts, addition of organic acids/bases, or addition of common inorganic acids/bases. The aqueous solution further comprises at least one water miscible organic solvent, which may be selected from the group including ethanol, methanol, DMSO, dioxane, DMF, NMP, etc. In another aspect, the organic solvent, preferably dioxane, is included at a concentration (v/v) of from 0 to 25%, preferably from 2-20%, more preferably from 5-15%.

Suitable metal chelators for use in the invention include a wide variety of known chelators including, for example, aminopolycarboxylic acids, such as, ethylenediaminetetraacetic acid (EDTA), diethylenetriamine pentaacetic acid (DTPA), nitrilotriacetic acid (NTA), N-2-acetamido-2-iminodiacetic acid (ADA), bis(aminoethyl)glycolether, N,N,N',N'-tetraacetic acid (EGTA), trans-diaminocyclohexane tetraacetic acid (DCTA), glutamic acid, and aspartic acid; and hydroxyaminocarboxylic acids, such as, for example, N-hydroxyethyliminodiacetic acid (HIMDA), N,N-bis-hydroxyethylglycine (bicine) and N-(trishydroxymethylmethyl) glycine (tricine); and N-substituted glycines, such as glycylglycine. Other suitable chelators include 2-(2-amino-2-oxocthyl) aminoethane sulfonic acid (BES) and deferoxamine (DEF). Suitable chelators used in the methods of the present invention include, for example, those that bind to metal ions in solution to render them unable to react with available $O_2$, thereby minimizing or preventing generation of •OH radicals which are free to react with and degrade the protein. Such chelators can reduce or prevent degradation of a protein that is formulated without the protection of a chelating agent.

Chelating agents used in the invention can be present in their salt form, e.g., carboxyl or other acidic functionalities of the foregoing chelators. Examples of such salts include salts formed with sodium, potassium, calcium, and other weakly bound metal ions. As is known in the art, the nature of the salt and the number of charges to be neutralized will depend on the number of carboxyl groups present and the pH at which the stabilizing chelator is supplied. As is also known in the art, chelating agents have varying strengths with which particular target ions are bound. In general, heavy metal ions are bound more strongly than their similarly charged lower molecular weight counterparts.

The chelator used in the methods of the present invention may also be selected from EDTA, EGTA, and other multivalent cation chelators known in the art. According to the methods of the invention, a metal chelator, preferably EDTA, is present at a concentration from 0.1 to 10 mM, preferably from 1-5 mM, more preferably from 1-3 mM.

Suitable hydrophilic polymers for use in the present invention include a wide variety of known polymers including, for example, polyethylene glycol, polypropylene glycol, and linear, branched and amino-reactive derivatives thereof. In one aspect of the invention, the amino-reactive derivative is selected from the group consisting of an aldehyde, a N-hydroxy succinimide, a PNP-carbonate, and a benzotriazole terminated hydrophilic polymer derivative. In a particular embodiment of the invention, the hydrophilic polymer, e.g. a PEG reagent, preferably a succinimidyl ester of PEG, more preferably mPEG-SPA, is contacted with insulin at a molar ratio (PEG:insulin) of about 10:1 to 1:1, preferably 3:1 to 1.2:1, more preferably 1.7:1 to 1.5:1. In another particular embodiment, the hydrophilic polymer and insulin protein are contacted at a temperature of about 4° C. to 50° C., preferably about 15° C. to 25° C.

In another embodiment, the invention further comprises the step of quenching the conjugation reaction prior to isolating the conjugate. This can be achieved by, for example, reducing the pH to about 1-4, preferably about 2-3, more preferably about 2.4 to 2.6. The isolation of the conjugate can then be achieved using standard techniques, such as ion exchange (e.g., cation exchange) chromatography, and the desired conjugate may be collected, concentrated, desalted and dried.

Use of Conjugated Bioactive Agents in Controlled Release Delivery Formulations

Conjugated bioactive agents, such as PEGylated insulin proteins, may be advantageously encapsulated in biodegradable polymer-based drug delivery formulations. PEGylated bioactive agents are encapsulated at higher concentration in the drug delivery formulation than the corresponding non-PEGylated bioactive agents. The release of PEGylated bioactive agents from biodegradable polymer drug delivery formulations shows less burst than for the corresponding non-PEGylated bioactive agents. The physical and chemical stability of PEGylated bioactive agents in biodegradable polymer drug delivery formulations is greater, and the antigenicity and immunogenicity are lower than for the corresponding non-PEGylated bioactive agents.

Biodegradable polymers for this application include, but are not limited to, poly(lactide)s, poly(glycolide)s, poly(d,l-lactide-co-glycolide)s, poly(caprolactone)s, poly(orthoester)s, copolymers of poly(esters) and poly(ethers), copolymers of poly(lactide) and poly(ethylene glycol) and the like.

Accordingly, protein-polymer (e.g., PEGylated insulin) conjugates of the present invention can be beneficially incorporated into biodegradable polymer drug delivery formulations including, for example, poly(d,l-lactide-co-glycolide) (PLGA) microparticles. This achieves higher encapsulation of the protein conjugate as compared to non-conjugated protein and also reduces burst (release over the first 24 hours). Moreover, conjugation with hydrophilic polymers, such as PEG, renders the conjugate soluble in certain organic solvents, simplifying the process of forming PLGA microspheres.

EXAMPLES

I. Preparation and Characterization of Site-Specific Peg-Insulin by One-Step Method Example 1

Preparation of $N^{\alpha B1}$-Methoxypoly (Ethylene Glycol)-Insulin Conjugates

One gram (172 µmol) of insulin ($Zn^{2+}$-insulin, Intergen Co.) was dissolved in 100 mL water with 2 mM EDTA at room temperature, and the solution's $pH_{app}$ was adjusted to 7 using dilute HCl. In another vessel 1.4 g (1.6 mol equivalents relative to insulin) of an activated PEG derivative [monomethoxypoly (ethylene glycol) succinimidyl propionate, mPEG-SPA, Shearwater Corp.] was dissolved in 10 mL dioxane at room temperature. The mPEG-SPA solution was then added to the insulin solution by direct injection and the reaction was allowed to proceed for 2 hr at room temperature. The reaction was then quenched by acidification with HCl ($pH_{app}$ 2.5) and the mixture was diafiltered [Amicon 8200 ultrafiltration apparatus fitted with a YM3 (3000 MWCO) membrane] against 0.02% ammonium bicarbonate. Then the reaction mixture was diafiltered against 1M acetic acid/7M urea/0.01M NaCl and concentrated to 10 mL prior to purification. The mPEG-PheB1-insulin derivative was isolated from the other reaction side-products (mPEG-GlyA1-insulin, mPEG-LysB29-insulin, di-mPEG-insulins, and tri-mPEG-insulins) using a FPLC system fitted with a SP Sepharose (Amersham Biosciences) cation-exchange column. The column was equilibrated with 1M acetic acid/7M urea containing 0.04M NaCl at a flow rate of 5 mL/min and the bound proteins were eluted using a NaCl-gradient (0.04M-0.12M) over 80 min. The eluate corresponding to the major peaks detected at 280 nm were collected and diafiltered against 0.02% $NH_4HCO_3$ to remove any low molecular weight impurities, then lyophilized and stored at −20° C. prior to characterization.

This same method was also used to prepare one conjugate having a lower molecular weight linear polymer (i.e., mPEG-SPA, $M_r$=2000 Da) and two higher molecular weight branched polymers (i.e., $mPEG_2$-SPA, $M_r$=10,000 Da) attached to the amino group of PheB1, and these two distinct conjugates were also characterized according to the techniques outlined below. The results confirm this approach can be successfully employed to prepare a wide variety of PEG-PheB1-insulin conjugates that differ only in the structure (i.e., linear or branched) or size (i.e., molecular weight) of the polymer attached to PheB1.

Example 2

FPLC/HPLC Assessment of Conjugate Purity

The purity of the mPEG-PheB1-insulin was analyzed using an analytical cation-exchange column (MonoS 5/5, Amersham Biosciences) under identical conditions to those used in the isolation procedure described above, except a flow rate of 1.0 mL/min was employed. An orthogonal technique (reversed-phase HPLC) was also used to verify the final purity of the conjugates. A Waters Alliance HPLC system was fitted with a Waters 996 photodiode array detector (PDA) and a Symmetry 300 (C18, 5 µm particle size, 4.6×250 mm) reverse phase column. Mobile phase A consisted of 0.1% TFA (trifluoroacetic acid) in MilliQ quality water and mobile phase B consisted of 95/5 ACN (acetonitrile)/$H_2O$ also containing 0.1% TFA. A linear gradient from 30-60% B over 15 min (2% B/min) was utilized and the elution of compounds was followed by detection at 276 nm. The purity of the mPEG-insulin is >95%.

Example 3

N-Terminal Protein Sequencing (Edman Degradation) Confirmation of Conjugate Identity N-terminal protein sequence analysis was utilized to determine the site of PEG conjugation, with the knowledge that the Edman degradation reaction will not proceed at any N-terminal amino group that is covalently bound to PEG. All samples were analyzed using an Applied Biosystems 477A Protein Sequencer (Pasadena, Calif.) through three degradation cycles. An N-terminal amino acid molar ratio of [GlyA1/PheB1]≈1 is indicative of conjugation to residue LysB29 (or none at all), a [GlyA1/PheB1]≈0 is indicative of conjugation to residue GlyA1, and [GlyA1/PheB1]≈30 is indicative of conjugation to residue PheB1. The result confirmed that the site of substitution was approximately 95% PheB1.

Example 4

Matrix-Assisted Laser Desorption Ionization (MALDI) Identification of Conjugate Molecular Weight This analytical characterization technique was chosen because it is a "soft-ionization" method meaning that it will not cause the PEG-insulin conjugates to break down during analysis. The instrument's output provides a quantitative measure of the mass/charge ratio of each sample; therefore the number of PEG chains attached to insulin should be easily determined from the overall difference in the molecular weights of the conjugates and unmodified insulin. All samples were run on a Perceptive Biosystems model DERP MALDI/TOF mass spectrometer operated in the linear mode and positive ions were monitored. The matrix for all samples was α-cyano-4-hydroxycinnamic acid and the 337 nm line of a nitrogen laser was used with at least 64 shots averaged for the final spectrum. Monomeric insulin had a calculated molecular weight of 5807.2 Da, and the number-average molecular weight of mPEG(5000)-SPA used in the conjugation reaction was 5129 Da. The mass spectra of the mPEG (5000)-insulin were consistent with the conclusion that only one mPEG chain was attached to insulin. In addition, the individual ion peaks consistently differed by 44 Da (the molecular weight of an ethylene oxide monomer unit). These results confirm that only one mPEG chain was attached to insulin in all of the conjugates prepared and that their polydispersity is solely due to the polydispersity intrinsic to PEG.

Example 5

Secondary Amine Formation in Coupling PEG to Insulin B1 Amino Terminus

F5000 PEG-insulin was prepared by reaction of the protein with an activated mPEG possessing a terminal aldehyde group. This reaction proceeds through a Schiff's base intermediate, which is subsequently reduced by sodium cyanoborohydride forming a stable secondary amine bond between the polymer and protein. The reaction was carried out as follows: a 2 mM EDTA/25 mM phosphate buffer was made and adjusted the pH to 6.0 with phosphoric acid. Insulin at 5.5 mg/mL (2 mL total volume) was dissolved in the phosphate buffer with the addition of 440 μL dioxane. Once the insulin was in solution 2 mL of a 10 mM NaCNBH$_3$ solution in water were added and then a 5× molar excess of mPEG(5000)-aldehyde (as a dry powder, Shearwater Corporation, Huntsville, Ala.) was added. Overall, the reaction mixture contained approximately 12.5 mM phosphate (pH 6.), 1 mM EDTA, 10% dioxane, 5 mM NaCNBH$_3$, 2.5 mg/mL insulin, and 10 mg/mL mPEG-aldehyde. The reaction was allowed to proceed overnight and the pH was found to be approx. 5.5 the following day. The reaction was quenched with addition of acetic acid to a pH of approximately 2. A small aliquot was analyzed using RP-HPLC. The major reaction species were determined as follows: approximately 70% of the reaction products are mono-PEGylated (r.t. 12.5 min.), with approximately 10% unreacted insulin (r.t. 9.8 min.) and 9% di-PEGylated (r.t. 13.8 min) insulin remaining. The mono-PEGylated fractions were pooled and dialyzed against 0.02% NH$_4$HCO$_3$ and lyophilized. MALDI-TOF analysis showed a single molecular mass corresponding to addition of one PEG-5000 chain to insulin. Edman degradation analysis showed that approximately 95% of the mono-PEGylated species were substituted at residue PheB1 and the remaining mono-PEGylated species (~5%) most likely substituted at residue GlyA1 because the amino group of LysB29 is 99.99% protonated (therefore unreactive) under the reaction conditions employed here.

II. Alternative Methods for Preparation of Site Specific Peg-Insulin Conjugates

Example 6

PEG-5000 Linked to B Chain Amino Terminus (F5000) Using Traditional Multi-Step Method Recombinant human insulin (Intergen Co.) was PEGylated at the PheB1 position utilizing a di-boc protected intermediate. Di-N$^{\alpha A1}$, N$^{\epsilon B29}$-t-boc-insulin (diboc-insulin) was synthesized according to Liu et al. 1997 (Liu et al., Bioconj. Chem. 8(5): 664-672, 1997). The mPEG (5000)-PheB1-insulin conjugate was prepared by the protocol of Hinds et al., 2000, supra.

The desired fraction isolated by FPLC was >98% pure based on chromatographic peak areas in reverse-phase HPLC and ion exchange FPLC. The purified product was further characterized by MALDI-TOF mass spectrometry and amino acid sequence analysis and was shown to be mono-substituted PEG at the B chain amino terminus, PheB1. The mPEG (5000)-PheB1-insulin conjugate (F5000) prepared and purified by this method was equivalent to the same conjugate made by the simpler and less time-consuming method of the present invention (Example 1).

Example 7

PEG-5000 Linked to B Chain Lys29 (K5000)

Recombinant human insulin (Intergen Co.) was PEGylated specifically at Lys29 of the B chain by the method of Hinds et al., 2000, supra. The desired FPLC fraction was >98% pure based on chromatographic peak areas in reverse-phase HPLC and ion exchange FPLC. The purified product was further characterized by MALDI-TOF mass spectrometry and amino acid sequence analysis, and was shown to be mono-substituted PEG at the B chain penultimate amino acid, LysB29. This same method was also used to prepare one conjugate having a lower molecular weight linear polymer (i.e., mPEG-SPA, M$_r$=2000 Da) and two higher molecular weight branched polymers (i.e., mPEG$_2$-SPA, M$_r$=10,000 or 20,000 Da) attached to the amino group of LysB29, and these three distinct conjugates were characterized according to the techniques outlined above. The results confirm this approach can be successfully employed to prepare a wide variety of PEG-LysB29-insulin conjugates that differ only in the structure (i.e., linear or branched) or size (i.e., molecular weight) of the polymer attached to LysB29.

III. Characterization of Site Specific Peg-Insulin Conformation, Activity, and Stability

Example 8

Assessment of Insulin Conformational Integrity Following Site-Specific PEGylation Circular dichroism spectroscopy in the far-ultraviolet range has been used to examine the conformation of insulin.

Usually the magnitudes of two negative minima are evaluated: 208 nm (α-helix) and 223 nm (β-sheet) in the analysis of insulin's conformation in aqueous environments. The far ultraviolet CD-band at 208 nm primarily arises from α-helicies formed from residues between B10-B19, A2-A6, and A13-19, while β-structure is the primary component of the far ultraviolet CD-band at 223 nm. The CD spectral characteristics of the samples confirm that attachment of mPEG to insulin at either residue PheB1 or LysB29, does not alter the overall conformation (secondary) of the conjugates as compared to $Zn^{2+}$-insulin.

Example 9

Pharmacodynamics of PEG-Insulin Conjugates

The effects of PEGylation on insulin pharmacodynamics were investigated. These studies were conducted to evaluate the in vivo biological activity (ability to lower serum glucose) of conjugate formulations containing PEG-insulins differing in site of substitution (positional isomers) or PEG molecular weight, relative to a commercially available insulin formulation (Humulin R, Lilly). Blood glucose levels were measured for fasted Sprague-Dawley rats after intravenous administration of F5000, K2000, K5000, K10000, or HumulinR®. The equivalent of 0.3 IU/kg (based on protein concentration and corrected for the weight of the PEG as appropriate; assumes 25 IU/mg protein) were dissolved in normal saline and administered by tail vein injection; N=6 per group. Blood was drawn before test article injection and at intervals over a period of 6 hrs post injection. Serum was isolated by standard procedure and glucose levels were measured using an Accucheck Advantage (Boeringer Ingelheim) glucose meter.

Figure 1A:
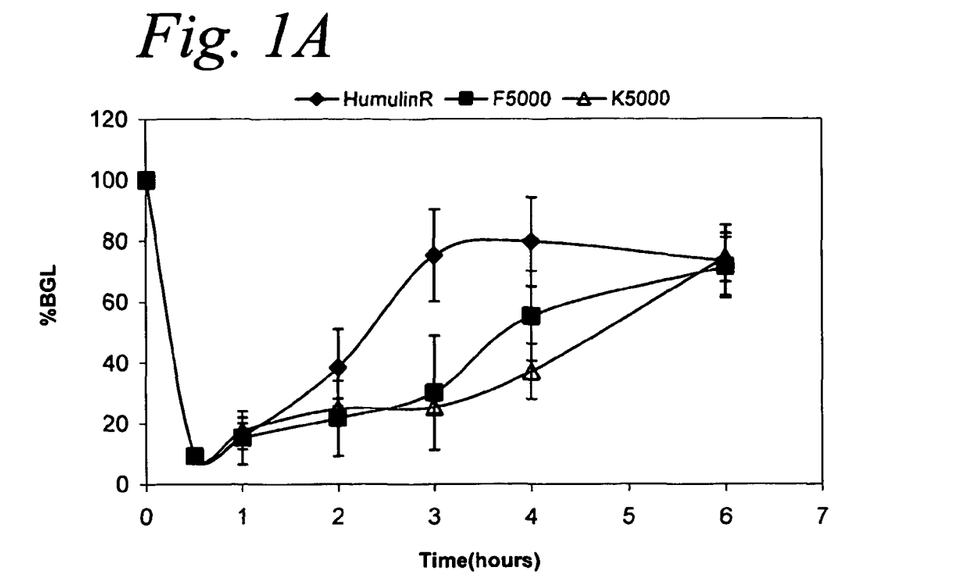
FIGS. 1A and 1B are graphs that depict the effects of site substitution (FIG. 1A) or polymer molecular weight (FIG. 1B) on the in vivo pharmacodynamics of PEG-insulin conjugates following intravenous injection to normal rats.
Figure 1B:
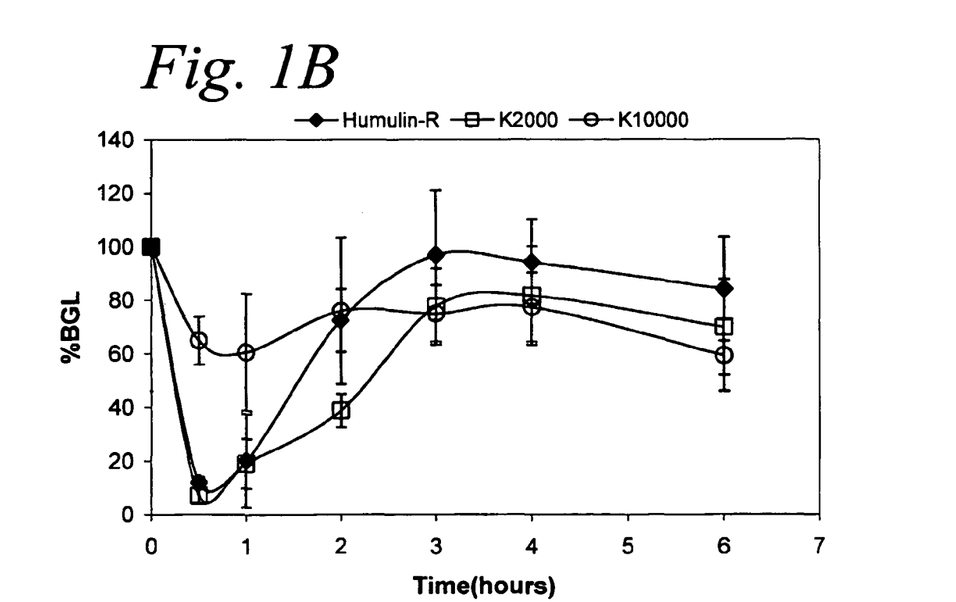

The results shown in FIGS. 1A and 1B reveal that F5000, K2000 and K5000 are all as effective in suppressing the glucose levels in normal rats as equivalent doses of normal human insulin. Interestingly, the K10000 conjugate did not reduce glucose levels to the same extent as the other test articles, but the conjugate's duration of action was observed to exceed 6 hours. Thus, the K10000 conjugate could be developed as a soluble alternative to conventional basal insulin suspensions for providing prolonged glucose suppression to diabetic patients.

Example 10

Physical Stability of Representative PEG-Insulin Conjugates

Figure 2A:
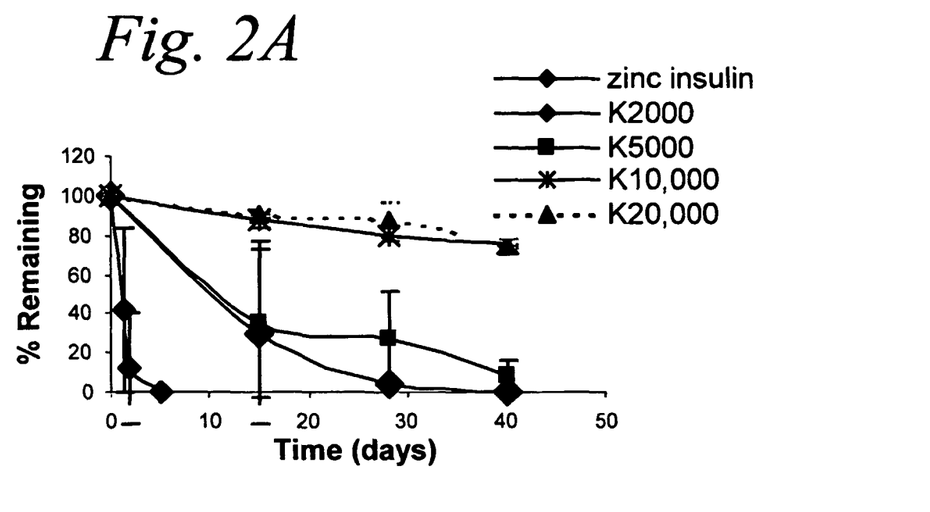
FIGS. 2A and 2B are graphs that depict the loss of soluble insulin due to physical aggregation for different molecular weight insulin-PEG conjugates with the same site of polymer attachment (FIG. 2A) and different sites of polymer attachment with the same molecular weight PEGF (FIG. 2B).
Figure 2B:
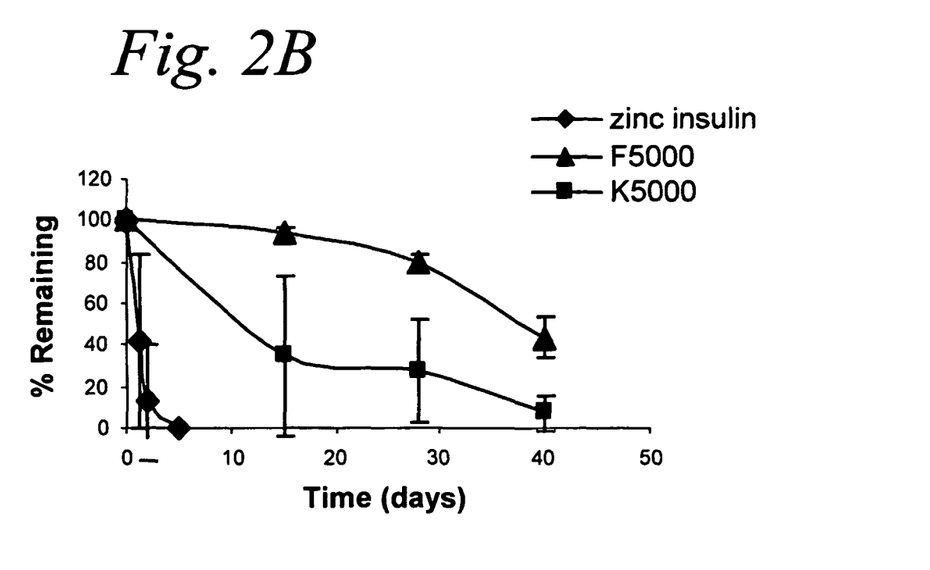
Figure 3:
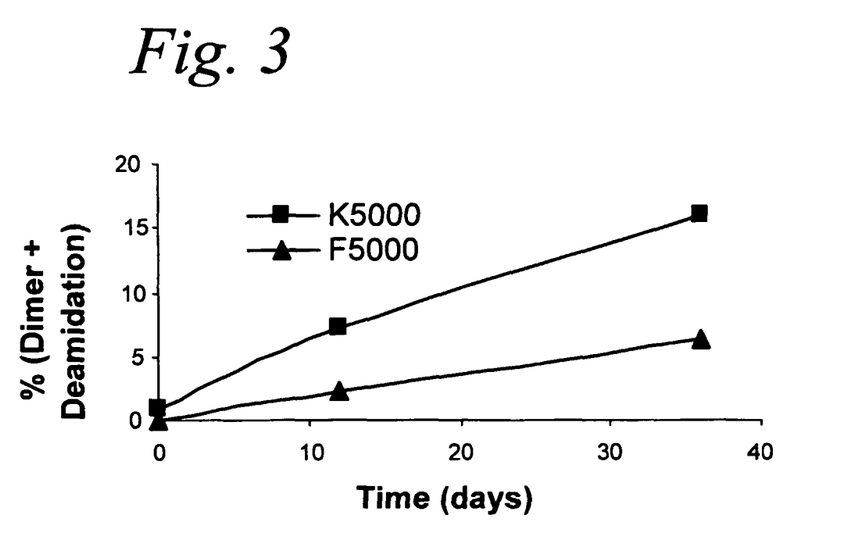
FIG. 3 is a graph that depicts the chemical stability of two mPEG(5000 Da)-insulin positional isomers.

An accelerated shake-test method was employed to investigate the physical stability of seven PEG-insulin conjugates (F2000, F5000, F10000, K2000, K5000, K10000, and K20000) and zinc insulin. This test is commonly described in the literature as providing an accurate measure of an insulin preparation's physical stability in an accelerated manner. For this assay, aqueous solutions of the protein (conjugates) were prepared in quadruplicate (1 mg/mL, phosphate buffered saline, pH 7.3, 0.02% sodium azide) and subjected to horizontal shaking (frequency of 100/min) at 37° C. Samples were withdrawn at predetermined time points, filtered (to remove insoluble aggregates) and analyzed by RP-HPLC to quantify the fraction of protein (conjugate) remaining in solution. FIG. 2 charts the decline of soluble protein as a function of time for each insulin derivative.

These data corroborate previous reports of insulin derivatives substituted at the PheB1-amino group possessing substantially higher (36-40×) physical stabilities and the LysB29-insulins were somewhat more stable (4-8×) than the native peptide. Previous research has shown that the increased resistance to fibrillation of PheB1-insulins is due to two complementary effects. The first effect is the specific steric blocking of the N-terminus in the B-chain by mPEG conjugation resulting in preventing this surface from participating in the hydrophobic interactions required for insulin fibril growth. The second contributing effect to PheB1-insulin's increased physical stability is nonspecific and steric in nature, and increases proportionally with polymer molecular weight. All of the LysB29-insulins exhibited increased physical stability relative to the native peptide, but not to the same extent as the conjugates substituted at PheB1 until the polymer molecular weight exceeded 10 kDa. This can be explained by the lack of LysB29's participation in fibrillation reactions, with any stabilizing effects caused by nonspecific steric-hindrance of the intermolecular interactions involved in fibrillation.

Example 11

Chemical Stability of Representative PEG-Insulin Conjugates

It is well documented that insulin (or insulin analogs) undergo a number of chemical decomposition reactions in aqueous solutions. For example, the C-terminal asparagine of insulin's A-chain decomposes according to a deamidation mechanism facilitated by a cyclic intermediate under acidic conditions. This highly reactive cyclic intermediate can also decompose by reaction with one of the N-terminal amino groups from a different insulin molecule via a transamination reaction mechanism.

The insulin-conjugates, F5000 and K5000, were incubated with horizontal shaking in PBS and 0.02% sodium azide at 37° C. At prescribed time points (0, 6, 12, 28, and 36 days), individual samples were withdrawn and then analyzed by RP-HPLC to determine the extent of deamidation and size exclusion chromatography to determine the extent of covalent dimerization.

IV. Preparation, Characterization, and Pharmacokinetics of Peg-Insulin Biodegradable Polymer Sustained Delivery Formulations Example 12

Encapsulation of PEG-Insulin in PLGA Microspheres

PEG-insulin F5000 (50 mg) was dissolved in 1 ml methylene chloride. The solution was added to a volume of 1 ml methylene chloride containing 150 mg PLGA 45:55 (lac:gly), 0.15 dl/g IV with acid end groups. The methylene chloride solution was added to 5 ml water containing 1% poly (vinyl alcohol) in a 15 ml centrifuge tube and vortex-mixed to form an emulsion. The emulsion was added to 100 ml of water containing 0.3% poly(vinyl alcohol) and stirred for 3 hrs to evaporate the methylene chloride. The hardened microspheres were collected by vacuum filtration on Whatman #1 filter paper and dried.

Example 13

Characterization of PEG-Insulin PLGA Microspheres

The PEG-insulin microspheres' surface morphology and particle size distribution were examined by scanning electron microscope and laser-light scattering particle size analysis, respectively. Analytical reverse phase HPLC was used to quantify the amount of PEG-insulin conjugate encapsulated within the polymer microspheres. Prior to HPLC analysis, a measured quantity of microspheres was dissolved in a volume of acetonitrile, and an equivalent volume of 0.1% TFA in water was added to precipitate the polymer and extract the conjugate into aqueous solution. K2000, K5000, K10000, K20000 and F5000-A were also encapsulated using this method. The results of these tests are collected in Table 1, which lists the PEG-insulin content in % (w/w) of the total microsphere and the encapsulation efficiency, defined as weight of PEG-insulin encapsulated/weight of PEG-insulin added initially. Relatively high drug content up to 28.3% and encapsulation efficiency, up to 100%, were achieved, making the product clinically useful due to reduced total dose required, and commercially attractive due to low losses of starting material. In addition, microspheres were prepared using polymers of varying lactide:glycolide ratios (50:50 and 72:25), molecular weights (6.5-24 kDa), intrinsic viscosities (0.09-0.27 dL/g), or terminal ester groups (methyl and lauryl), with a wide range of drug loadings (5-35 wt %).

TABLE 1

Characteristics of representative PEG-insulin microsphere preparations

| Conjugate | Coreload (wt %) | Encapsulation Efficiency (wt %) | In vitro release (%) | |
|---|---|---|---|---|
| | | | Initial burst | Total |
| K2000 | 24 | 96 | 6 | |
| K5000 | 24 | 96 | 2 | |
| K10000 | 19 | 76 | 80 | |
| K20000 | 14 | 56 | 80 | |
| F5000 | 24 | 96 | 2 | |
| F5000-A | 21 | 85 | 20 | 97 |

Microspheres were prepared with PLGA (45:55 L:G, 0.15 dL/g, acid end group) to a nominal core load of 25 wt %.

Example 14

Figure 4:
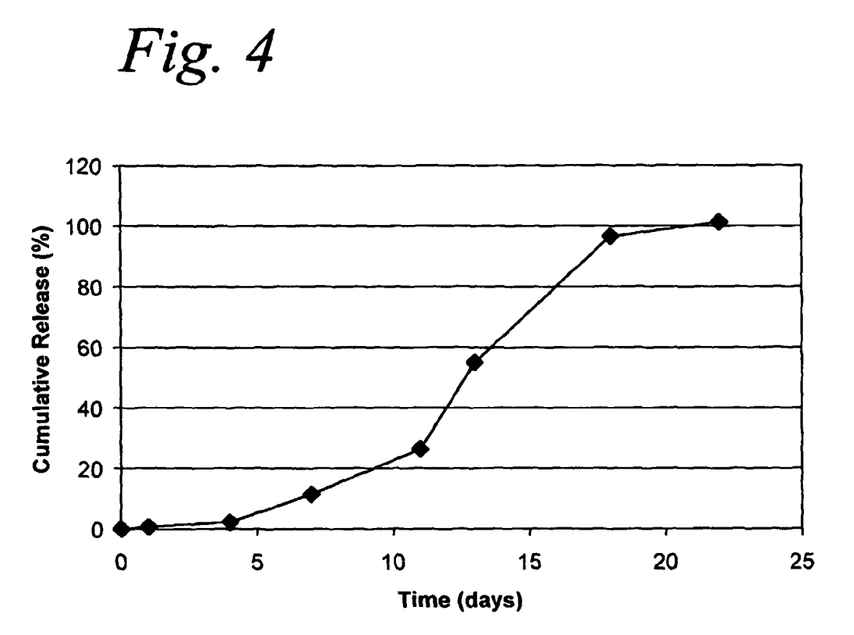
FIG. 4 is a graph that depicts the cumulative in vitro release of F5000 (PEG-insulin) from PGLA microspheres.

In Vitro Release of the PEG-Insulin Microsphere Formulation Used in Animal Experiments A sample of 15 mg F5000 PEG-insulin microspheres (14.1% drug content, PLGA 45:55, 0.15 dl/g IV, acid end groups) was suspended in 1.5 ml phosphate buffered saline (pH 7.4, 0.02% sodium azide and 0.02% TWEEN-20™) and incubated at 37° C. The supernatant was withdrawn at intervals and analyzed by RP HPLC for released PEG-insulin. The buffer was replaced with fresh PBS and the incubation continued. The data were analyzed for cumulative release as a function of incubation time (FIG. 4). Less than 1.0% of the PEG_insulin is released in the first day and over 95% is released within 18 days. The low "burst" release, high total release and duration over approximately a two-week period are highly desired features of a sustained release insulin formulation.

Other preparations made by the method of Example 12 using F5000 with different biodegradable polymers and also using K5000 PEG-Insulin and F5000-A conjugates also gave one-day release values of between 0 and 7.5% and sustained release durations up to 60 days.

Example 15

Figure 5:
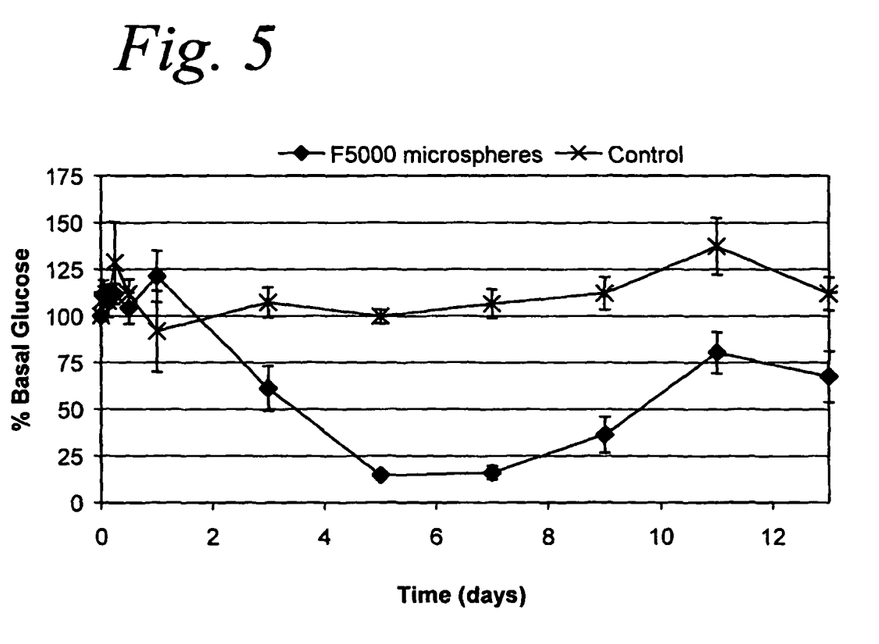
FIG. 5 is a graph that depicts in vivo pharmacodynamics of F5000 (PEG-insulin) microspheres following subcutaneous administration to diabetic rats.
Figure 6:
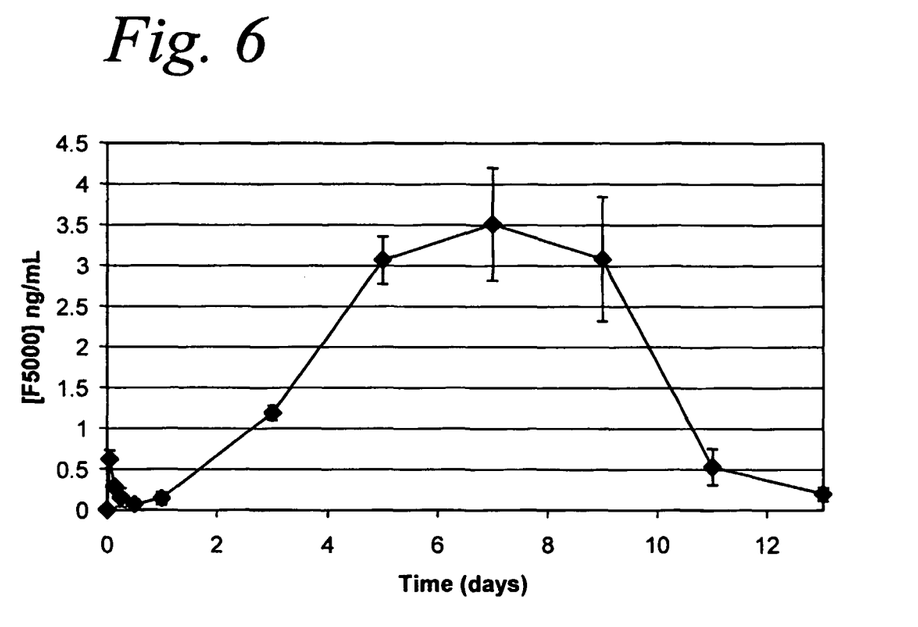
FIG. 6 is a graph that depicts in vivo pharmacokinetics of F5000 (PEG-insulin) microspheres following subcutaneous administration to diabetic rats.

In Vivo Pharmacodynamics and Pharmacokinetics for F5000 PEG-Insulin PLGA Microspheres F5000 PEG-insulin in microspheres composed of PLGA 45:55. 0.15 dl/g IV, acid end groups (14.1% coreload) were tested for glucose suppression and for F5000 pharmacokinetics in diabetic rats. Male SD rats (~250 g) were rendered diabetic by subcutaneous administration of 40 mg/kg streptozotocin (Sigma, St. Louis, Mo.) dissolved in isotonic citrate buffer (10 mM, pH 4.5) one day prior to test article administration (Junod, A. et al., J. Clin. Invest., 48: 2129-2139, 1969). Animals were then treated with PEG-insulin microspheres (~11 mg/rat, corresponding to 3 mg insulin equivalent/kg body weight) suspended in 2.5% sterile carboxymethylcellulose (CMC) or saline (negative control) and blood was withdrawn at prescribed time points for isolation of serum and subsequent analysis of glucose (PD) and F5000 (PK) levels. FIGS. 5 and 6 show the serum glucose levels and serum PEG-insulin levels over a 13-day period (data are means+/– SE). FIG. 5 shows that blood glucose levels are 100% or above (within error of measurement) for the control diabetic rats throughout the experiment, as expected. For the PEG-insulin microsphere treated diabetic rats, the blood glucose level drops to levels below 60% of pretreatment levels after 3-days and remain suppressed for another 7 days.

FIG. 6 shows a negligible initial burst release ($C_{max}$=0.62 ng/mL) of PEG-insulin was detected shortly after (t=1 h) microsphere injection. Then beginning 24-hours post-injection, the treated group's PEG-insulin levels rose steadily over 2 days to therapeutic levels (~1-3.5 ng/mL) that were maintained for approximately 7 days, while the negative control group's F5000 serum levels were below the limits of detection at all times. These data, taken together, indicate that the conjugate's biological activity was preserved during the microsphere fabrication process and maintained during the weeklong release period following microsphere injection. Importantly, similar amounts of initial PEG-insulin burst release were found in the in vitro (FIG. 4, <0.5% released in the first day) and in vivo (FIG. 6, $AUC_{0-1d}/AUC_{0-13d}$=0.7% experiments). In addition, evaluation of the data illustrated in FIGS. 5 and 6 suggests a pharmacokinetic/pharmacodynamic (PK/PD) correlation exists for this example.

EQUIVALENTS

Those skilled in the art will recognize, or be able to ascertain using no more than routine experimentation, many equivalents to the specific embodiments of the invention described herein. Such equivalents are intended to be encompassed within and covered by the following claims.

What is claimed:

1. A method for preparing a site-specific insulin-PEG conjugate comprising:
  (a) contacting insulin protein with PEG in an aqueous solution in the presence of at least one organic solvent selected from the group consisting of ethanol, methanol, DMSO, dioxane, DMF, and NMP and at least one metal chelator selected from the group consisting of metal ion chelators, EDTA, deferoxamine (DEF), diethylenetriamine pentaacetic acid (DTPA), and bis(aminoethyl) glycolether N,N,N',N'-tetraacetic acid (EGTA), to form the site-specific insulin-PEG conjugate by a predominant reaction of the insulin protein at residue PheB1 without protecting the insulin protein at GlyA1 and LysB29 residues, and
  (b) isolating the conjugate.

2. The method of claim 1, wherein the insulin protein comprises human insulin.

3. The method of claim 1, wherein the PEG comprises an amino-reactive PEG derivative selected from the group consisting of an aldehyde, a N-hydroxy succinimide, a PNP-carbonate, and a benzotrizole terminated hydrophilic polymer.

4. The method of claim 1, wherein the PEG and insulin protein are contacted at a molar ratio of about 10:1-1:1.

5. The method of claim 1, wherein the organic solvent is present at a concentration of about 0.1 to 10%.

6. The method of claim 1, wherein the insulin protein and the PEG are contacted at a pH of about 5.0-7.5.

7. The method of claim 1, wherein the metal chelator is present at a concentration of about 0.1-10 mM.

8. The method of claim 1, wherein the insulin protein and the PEG are contacted at a temperature of about 4-50° C.

9. The method of claim 1, wherein the method further comprises the step of quenching formation of the conjugate prior to the isolating of the conjugate.

10. The method of claim 1, further comprising the step of:
  (c) encapsulating the isolated conjugate in a biodegradable polymer.

* * * * *